United States Patent
Dyrsting et al.

[11] Patent Number: 5,595,977
[45] Date of Patent: Jan. 21, 1997

[54] SALTS OF AMINO GLYCOSIDES

[75] Inventors: Hjarne Dyrsting, Virum; Torben Koch, København, both of Denmark

[73] Assignee: Dumex-Alpharma A/S, Copenhagen S, Denmark

[21] Appl. No.: 141,625

[22] Filed: Oct. 27, 1993 DK

[51] Int. Cl.⁶ .............. A61K 31/70; C07H 5/00
[52] U.S. Cl. .............. 514/39; 514/35; 514/36; 514/37; 514/38; 514/40; 514/41; 514/53; 536/13.6; 536/13.7; 536/13.8; 536/14; 536/16.8
[58] Field of Search .............. 514/35, 36, 37, 514/38, 39, 40, 41, 53; 536/13.6, 13.7, 13.8, 14, 16.8

[56] References Cited

U.S. PATENT DOCUMENTS 5,116,821   5/1992   Randall et al. .............. 514/25

FOREIGN PATENT DOCUMENTS 0403048   12/1990   European Pat. Off. .
WO95/14483   6/1995   WIPO .

Primary Examiner—Elli Peselev
Attorney, Agent, or Firm—Watov & Kipnes

[57] ABSTRACT

The present invention relates to novel amino glycoside salts of sucrose-octa-O-sulfonic acid of formula I:

$$([\text{sucrose-octa-O-sulfonic acid}^{8-}]\text{-}[R\text{-}(NH_3^+)_x]_y\text{-}M_z^{n+}) \quad (I)$$

$(x \cdot y) + (z \cdot n) = 8$ $x \cdot y \in N | [4 \leq x \cdot y \leq 8]$, wherein N is the set of natural numbers, $x \in Z | [4 \leq x \leq 6]$, wherein Z is the set of integers $z \in N | [0 \leq z \leq 4]$, $n \in Z | [1 \leq n \leq 3]$, wherein R is a sugar moiety of an amino glycoside and M is a metal ion or an ammonium ion, said compounds being useful for treating ulcerations of the stomach and duodenum.

6 Claims, No Drawings

SALTS OF AMINO GLYCOSIDES

The present invention relates to novel amino glycoside salts with sucrose-octa-O-sulfonic acid.

These novel salts may be used for the treatment of ulcerations in the stomach and/or the duodenum, preferably caused by *Helicobacter pylori*.

*Helicobacter pylori* (previously known as *Campylobacter pylori*) is a helical Gram-negative organism which is present in the stomach mucosa. Many recent tests have shown a clear correlation between the presence of *H. pylori* in the stomach mucosa and histologically shown gastritis. On the basis of this, much seems to indicate that this organism is wholly or partially responsible for the development of gastritis with ensuing ulcerations (Scand. J. Gastroenterol. 1988 (23) suppl. 142, pp. 93–100).

*H. pylori* is sensitive to a number of known antimicrobial substances in vitro. Furthermore, several publications disclose that the treatment of gastritis with antimicrobial agents, such as β-lactames (e.g. amoxicillin) or bismuth salts results in the eradication of *H. pylori* in vivo (Antimicrobial Agents and Chemother. 1993, pp. 1184–86).

The traditional treatment of ulcerations in the stomach or the duodenum consists in administering acid neutralising agents or preparations of the anti-histamin $H_2$-inhibitor type which reduces the production of acid, (e.g. ranitidine, cimetidine, etc.) and acid pump-inhibitors, such as omeprazole. This treatment as such is efficient, but it has a short-term effect only as, in almost every case, there is a relapse due to the very cause of the ulcer ailment, *H. pylori* infection, still being present.

Today the optimum treatment of ulcerations caused by *H. pylori* comprise administration of bismuth subcitrate, amoxicillin and metronidazole. This treatment cures 60–90% of the patients (Ann. Rev. Med. 1992 (43) p. 142).

However, there are certain side effects associated with this therapy:

Bismuth subcitrate may cause constipation and in large doses it may be neurotoxic.

Amoxicillin and metronidizole are systemically acting antibiotics which may cause the development of allergy or resistance and influence the microflora in the colon.

Therefore, there is much need for a preparation for local treatment of *H. pylori* infections in the stomach and the duodenum.

Amino glycosides form a group of antibiotics which have a good in vitro effect on *H. pylori*. The following MIC-values are known from the literature:

TABLE 1

|  | Average MIC 90 range |
|---|---|
| AMIKACIN | 0.5 |
| GENTAMYCIN | 0.04–1 |
| KANAMYCIN | 0.04–2 |
| STREPTOMYCIN | 0.04–1.28 |
| TOBRAMYICN | 0.04–0.64 |

(Antimicrobial Agents and Chemother., 1986, pp. 510–511, J. Anti-microbial Chemother. 1986, 17, pp. 309–314, Scand. J. Gastroenterol., 1988, 23 (suppl. 142), pp. 93–100).

So far amino glycosides have not been found to be suitable for use in the treatment of *H. pylori* infections. The reason is that they are not absorbed in case of peroral administration in therapeutic doses. Amino glycosides may be administered parenterally but this is impractical in the present case as these substances have known oto- and nefro-toxic properties. When known readily soluble salts of amino glycosides are administered orally, they do not influence the stomach and duodenum mucosae due to their poor tissue penetration and thus they will not be capable of eradicating *H. pylori*. On the contrary, they will have a considerably influence on the colon microflora and may cause diarrhoea.

β-D-fructofuranosyl-α-D-glucopyranoside octakis (hydrogen sulfate) (in the following referred to as sucrose-octa-O-sulfonic acid) is produced by sulphating sucrose with sulphur trioxide in pyridine. In this process eight hydroxy groups in sucrose are esterified with eight molecules of sulphuric acid under formation of semiesters. Sucrose-octa-O-sulfonic acid forms well crystallized salts with Na, K, Cs, Rb and ammonium. (Chem. Pharm. Bull., 1980, 28 (2), pp. 638–341).

None of these salts have been found suitable for practical use. The only salt of the sucrose-octa-O-sulfonic acid which is used for medical therapy is the aluminium salt produced by treatment of sucrose-octa-O-sulfonic acid with aluminium hydroxide (U.S. Pat. No. 3,432,489 to Chugai, 1969) and it is known under the name of sucralfate having the gross formula $C_{12}H_{54}Al_{16}O_{75}S_8$. (Merck Index 11th Edition, pp. 1400–1401).

Sucralfate is widely used for the treatment of gastric ulcers. Peroral administration of tablets or a suspension causes sucralfate to react with the acidic gastric juice under formation of a sticky gel which adheres to the mucosa and forms a protective layer, especially on the ulcerated areas.

The effect of sucralfate is largely ascribed to the high content of aluminium hydroxide ions which act as acid neutralizers and absorb pepsin and bile salts. (Clin. Gastroenterol. 1981, 3 (suppl. 2), pp. 117–127).

No other salts of the sucrose-octa-O-sulfonic acid has hitherto been found suitable for use in the treatment of ulcer ailments.

EP 403.048 to Warner-Lambert Co. discloses mixtures of sucralfate with anti-ulcer medicaments which per se either have low solubility or, where readily soluble, are available in a controlled-release form by means of suitable adjuncts. Among said anti-ulcer agents are antimicrobial substances, such as bismuth salts and antibiotics which may be genta-, strepto-, kana- and neomycins. These amino glycosides, however, are not mentioned in any of the examples. Only mechanically produced mixtures of sucralfate and medicaments are disclosed. No other sucrose-octa-O-sulfonic acid compositions are disclosed and a chemical interaction between the sucralfate and the basic medicaments described is not obvious from the EP patent.

WO 92/18143 to Smith-Kline Beecham PLC also discloses a physical mixture of sucralfate and antibiotics of the bacteriocins-type, nisin, gramicidin and tyrothricin are particularly preferred. Nor does this publication disclose or render probable a chemical interaction between sucrose-octa-O-sulfonic acid and the basic antibiotic.

It is an object of the invention to provide novel salts of amino glycosides which are well suitable for local treatment of gastritis and/or ulcerations in the stomach and/or the duodenum caused by *H. pylori*.

It has surprisingly been found that sucrose-octa-O-sulfonic acid and amino glycosides form salts in stoichiometric ratios and that said salts have valuable pharmaceutical properties.

Amino glycosides belong to the group of sugars having a certain number of amino groups, preferably 4, 5 or 6. They are obtained by fermentation of various Streptomyces- or Micromonospora-species. Due to the many hydrophilic hydroxy or amino groups in the amino glycosides said substances and the salts thereof are readily soluble in water.

The known salts, except from the aluminium salt, of sucrose-octa-O-sulfonic acid are also readily soluble.

As the amino glycosides have 4, 5 or 6 cation-forming amino groups and sucrose-octa-O-sulfonic acid have 8 anion-forming sulfate groups, the skilled person will not readily expect that the amino glycosides will form well defined salts with sucrose-octa-O-sulfonic acid. It should namely be taken into consideration that both amino glycosides and sucrose-octa-O-sulfonic acid have complex spatial constructions which means that the establishment of so strong ion bondings between e.g. the 4 amino groups in kanamycin A and the 8 sulfate groups in sucrose-octa-O-sulfonic acid that the resulting substance has low solubility in water is not immediately predictable.

It has now been found that most known amino glycosides with a content of 4 or 5 or 6 amino groups and sucrose-octa-O-sulfonic acid form salts with the following general formula I:

$$([\text{sucrose-octa-O-sulfonic acid}^{8-}] - [R - (NH_3^+)_x]_y - M_z^{n+}) \quad (I)$$
$$(x \cdot y) + (z \cdot n) = 8$$
$$\wedge$$
$$x \cdot y \in N[4 \leq x \cdot y \leq 8], \text{ wherein } N \text{ is the set of natural numbers}$$
$$\wedge$$
$$x \in Z[4 \leq x \leq 6], \text{ wherein } Z \text{ is the set of integers}$$
$$\wedge$$
$$z \in N[0 \leq z \leq 4]$$
$$\wedge$$
$$n \in Z[1 \leq n \leq 3],$$

wherein R is the sugar moiety of an amino glycoside and M is an element capable of forming a cation, preferably a metal ion or an ammonium ion.

It has also been found that it is possible to form well defined compounds between sucrose-octa-O-sulfonic acid and amino glycoside and then to produce neutral salts by introducing cations. The following pharmaceutically acceptable cations are preferred:

Alkaline metal ions, such as $Na^+$ and $K^+$, or $NH_4^+$,

Alkaline earth metal ions, such as $Ca^{2+}$ and $Mg^{2+}$, or $Al^{3+}$.

The novel salts produced according to the invention have comparatively low solubility in water. When stirred into water the novel salts form oily gels with a high degree of affinity to e.g. the inside surface of the glass container wherein the precipitation is effected. Such precipitation will also occur on biological surfaces such as the mucosae of the stomach or the duodenum.

Furthermore, the novel salts will decompose in aqueous solutions at a pH of 3 or less. Therefore, the novel salts will be suitable for the treatment of ulcerations caused by *H. pylori* in the stomach and the duodenum.

By peroral administration in a suitable pharmaceutical formulation the novel salts will precipitate in the form of a gel which covers the mucosae of the stomach and/or the duodenum if the stomach pH is neutral or slightly below.

Upon consumption of food, the stomach will secernate hydrochloric acid. *H. pylori* is sensitive to acid, such as gastric acid, but it has developed a protective measure. This protective measure consists in *H. pylori* producing an enzyme, urease, which will split urea into ammonia and $CO_2$. The ammonia thus formed neutralizes the gastric acid.

When the areas of the stomachs which are infected with *H. pylori* come into contact with the salts produced according to the invention, the ammonia formed will cause ion exchange with the amino glycoside portion of said salts and thus release the amino glycoside which subsequently kills the *H. pylori*.

If the ammonia thus formed is not sufficient to neutralize the gastric acid, a corresponding ion exchange effect will occur as the gastric acid will release the amino glycoside from the novel salts.

The novel salts of amino glycosides and sucrose-octa-O-sulfonic acid are produced in a manner known per se. They are particularly advantageously produced by allowing the aqueous solution of the amino glycoside bases to titrate with an aqueous solution of sucrose-octa-O-sulfonic acid to obtain the desired stoichiometric ratio.

If it is desired to produce salts in a 1:1 ratio it is necessary to neutralise the excess sulfate groups in the sucrose-octa-O-sulfonic acid with suitable cations, such as Na, Ca, Mg or Al. In many instances, the salts thus formed will crystallise spontaneously. If this is not the case the salt may be obtained by evaporation, optionally to dryness, or by freeze drying, or by addition of a solvent which is miscible with water, such as MeOH or EtOH.

The novel salts may also be produced by direct reaction of an aqueous solution of a salt of sucrose-octa-O-sulfonic acid with an acid addition salt of an amino glycoside.

The amino glycosides used are preferably selected from among the following substances:

Amikacin, apramycin, arbekacin, bambermycins, butirosin, dibekacin, dihydrostreptomycin, fortimicin, gentamicin, isepamicin, kanamycin, micronimicin, neomycin, netilmicin, paromycin, ribostamycin, sisomicin, streptomycin, tobramycin.

Amikacin, gentamicin, kanamycin, neomycin, streptomycin and tobramycin are particularly preferred.

The novel salts according to the invention may be formulated in a known manner, e.g. in the form of tablets which may optionally be dispersible in water, capsules, powders, aqueous suspensions, syrups, etc.

EXAMPLE 1

Sucrose-octa-O-sulfonic acid 60 g (50 mmol) of sodium sucrose-octa-O-sulfonic acid (produced in accordance with J. Chem. Soc. Faraday Trans., 1981, 77, pp. 629–639) are dissolved in 200 ml of water and cation exchanged on Amberlite® IR 120 ($H^+$). The combined eluates are diluted to 1 liter corresponding to an 0.05 M solution.

The resulting solution is used in Examples 2 through 7.

EXAMPLE 2

Kanamycin A salt of sucrose-octa-O-sulfonic acid 17 g (25 mmol) of kanamycin A sulfate (Maiji Seika Kaisha Ltd., Tokyo, JP) are dissolved in 100 ml of ion exchanged water. The solution is eluated through an anionic exchanger, Amberlyst A26® ($OH^-$). The combined eluates are evaporated on a rotary evaporator to 100 ml and are titrated with an 0.05M solution af sucrose-octa-O-sulfonic acid (from Example 1) to a pH of 5.0. The product precipitates as a syrup. The above liquid is decanted. To the syrup is added 250 ml of EtOH and stirring is effected for 3 hours thereby effecting crystal precipitation.

The crystals are filtered off, washed with 2×25 ml of EtOH and vacuum dried over Sicapent at 45° C.

Yield: 20 g~82%.

DSC (Differential Scanning Calorimetry): The substance pyrolyses within the interval ranging from 180° to 195° C. and exhibits no melting point.

FTIR (Fourier Transformation Infra Red Spectroscopy): The spectre is almost identical to that of the substance of Example 6.

HPLC shows that the stoichiometric composition is a kanamycin: sucrose-octa-O-sulfonic acid ratio of 2:1.

EXAMPLE 2a: Small-scale dissolution test 250 mg of kanamycin salt of sucrose-octa-O-sulfonic acid in 25 ml of ion-exchanged water, 5% $NaH_2PO_4$ puffer with a pH=3 and 0.01 M HCl, respectively, at 37°±0.5° C. show that the substance has low solubility in water and only dissolves by ion exchange. The solubility is thus proportional with the ion activity.

EXAMPLE 3

The gentamycin salt of sucrose-octa-O-sulfonic acid 735 mg (1 mmol) of Gentamycin sulfate (Sigma, G-3632, 648 µg/mg) are dissolved in 25 ml of ion exchanged water. The solution is eluated through an anion exchanger such as in Example 2. The combined basic eluates are titrated with an 0.05M solution af sucrose-octa-O-sulfonic acid (from Example 1) to a pH of 6.5. Evaporation to about 5 ml which are triturated with 75 ml of EtOH and stirring is maintained for three hours which results in crystal precipitation.

The crystals are separated off, washed with 2×10 ml of EtOH and vacuum dried over Sicapent at 45° C.

Yield 950 mg~98%.

DSC: The substance pyrolyses in the interval of 210°14 215° C. and shows no melting point.

FTIR: Almost identical with that of the substance of Example 6.

EXAMPLE 4

The neomycin salt of sucrose-octa-O-sulfonic acid 910 mg (1 mmol) of neomycin sulfate (Sigma, N-1876, 657 µg/mg) are dissolved in 25 ml of ion exchanged water. The solution is eluated through an anion exchanger, such as in Example 2. The combined eluates are titrated with an 0.05M solution of sucrose-octa-O-sulfonic acid (from Example 1) to a pH of 6.5. Evaporation to about 5 ml which are triturated with 75 ml of EtOH and stirring is maintained for three hours which leads to crystal precipitation.

The crystals are filtered off, washed with 2×10 ml of EtOH and vacuum dried over Sicapent at 45° C.

Yield 1 g~90%.

DSC: The substance pyrolyses in the interval of 190°–210° C. and shows no melting point.

FTIR: Almost identical with that of the substance of Example 6.

EXAMPLE 5

The streptomycin salt of sucrose-octa-O-sulfonic acid 1550 mg (1 mmol) of streptomycin sulfate (Sigma, S-6501, 766 units/mg) are dissolved in 25 ml of ion exchanged water. The solution is eluated through an anion exchanger, such as in Example 2. The recovered eluates are titrated with an 0.05 M solution of sucrose-octa-O-sulfonic acid (from Example 1) to a pH of 6.5. Evaporation to about 5 ml which are triturated with 75 ml of EtOH and stirring is maintained for three hours which leads to crystal precipitation.

The crystals are filtered off, washed with 2×10 ml of EtOH and vacuum dried over Sicapent at 45° C.

Yield 1,5 g~91%.

DSC: The substance pyrolyses in the interval of 200°–210° C. and shows no melting point.

EXAMPLE 6

The tobramycin salt of sucrose-octa-O-sulfonic acid 500 mg (1 mmol) of tobramycin base (Sigma, T-4014, 941 µg/mg) are dissolved in 25 ml of ion exchanged water and are titrated with an 0.05 M solution of sucrose-octa-O-sulfonic acid (from Example 1) to a pH of approximately 6.5.

The emulsion thus formed is evaporated to about 5 ml and is triturated with 75 ml of EtOH and stirring is maintained for three hours which results in crystal precipitation. The crystals are filtered off, washed with 2×5 ml of EtOH and vacuum dried over Sicapent at 45° C.

Yield 650 mg~68%.

DSC: The substance pyrolyses in the interval of 215°–230° C. and shows no melting point.

HPLC shows that the stoichiometric composition is a tobramycin: Sucrose-octa-O-sulfonic acid ratio of 1.6:1.

EXAMPLE 7

Kanamycin/aluminium salt of sucrose-octa-O-sulfonic acid

Is produced by admixing equimolar amounts of sucrose-octa-O-sulfonic acid with kanamycin A-base. pH is subsequently adjusted to 5.2 with a slurry of $Al(OH)_3$ in water. The resulting gel is evaporated in a rotation evaporator to form an amorphous powder.

The production of corresponding salts with NaOH, $Ca(OH)_2$ and $Mg(OH)_2$ is carried out analogously with Example 7.

The following applies to all of the substances of Examples 2 through 7:

The produced reaction with water is a swelling reaction whereby a sticky substance or syrup is formed. The absorption of water occurs to a certain point where the particles have become an oily, viscous fluid which has comparatively low solubility in water. When applying such a drop on smooth skin a membrane is formed which has low solubility in water and which may only be removed by intensive scrubbing with water. By rinsing with ion-containing water the membrane is gradually dissolved until it disappears completely.

EXAMPLE 8

The production of kanamycin salt of sucrose-octa-O-sulfonic acid with Na-sucrose-octa-sulfate as starting substance.

7.75 g (10 mmol) of kanamycin A-sulfate dissolved in 50 ml of water is admixed with 6.5 g (5 mmol) of sodium sucrose-octa-sulfate, $C_{12}H_{14}S_8O_{35}Na_8$, $8H_2O$, produced in accordance with Example 1.

The mixture is dialysed until the ion strength of the washing water is constant, at this point kanamycin-octa-sulfate is dissolved, and the solution becomes milky.

The emulsion is evaporated to about 25 ml and triturated with 250 ml of ethanol whereby crystallisation occurs. Stirring is maintained for 3 hours and crystals are filtered off and dried as described under Example 2.

Yield 9,55 g~98%.

Analysis of the substance gives the same results as under Example 2.

We claim:

1. A compound of the formula (I):

$$([\text{sucrose-octa-O-sulfonic acid}^{8-}]\text{-}[R\text{-}(NH_3^+)_x]_y\text{--}M_z^{n+}) \quad (I)$$

wherein $(x \cdot y) + (z \cdot n) = 8$ $x \cdot y \in N | [4 \leq x \cdot y \leq 8]$, wherein N is the set of natural numbers, $x \in Z | [4 \leq x \leq 6]$, wherein Z is the set of integers $z \in N | [0 \leq z \leq 4]$, $n \in Z | [1 \leq n \leq 3]$, wherein R is a sugar moiety of an amino glycoside and M is selected from the group consisting of alkali metal ions, alkaline earth metal ions, an aluminum ion and an ammonium ion, or a pharmaceutically acceptable salt thereof.

2. The compound according to claim 1, wherein the amino glycoside is selected from the group consisting of kanamycin A, gentamicin, neomycin, netilmicin, streptomycin and tobramycin.

3. A compound according to claim 1 selected from the group consisting of:

[sucrose-octa-O-sulfonic acid]- [kanamycin A]$_2$,

[sucrose-octa-O-sulfonic acid]- [gentamicin]$_2$,

[sucrose-octa-O-sulfonic acid]- [neomycin]$_{1,3}$,

[sucrose-octa-O-sulfonic acid]- [netilmicin]$_{1,6}$,

[sucrose-octa-O-sulfonic acid]- [streptomycin]$_{1,6}$, and

[sucrose-octa-O-sulfonic acid]- [tobramycin]$_{1,6}$.

4. A pharmaceutical composition comprising a gastritis or ulceration treating effective amount of at least one compound of claim 1 and a pharmaceutically acceptable carrier or diluent.

5. A method of treating gastritis and ulcerations caused by *H. pylori* in at least one location selected from the stomach and the duodenum in a warm-blooded animal, comprising administering to said warm-blooded animal a gastritis treating or ulceration treating effective amount of a compound of formula I:

$$([\text{sucrose-octa-O-sulfonic acid}^{8-}]\text{-}[R\text{-}(NH_3^+)_x]_y\text{--}M_z^{n+}) \quad (I)$$

wherein $(x \cdot y) + (z \cdot n) = 8$ $x \cdot y \in N | [4 \leq x \cdot y \leq 8]$, wherein N is the set of natural numbers, $x \in Z | [4 \leq x \leq 6]$, wherein Z is the set of integers $z \in N | [0 \leq z \leq 4]$, $n \in Z | [1 \leq n \leq 3]$, wherein R is a sugar moiety of an amino glycoside and M is selected from the group consisting of alkali metal ions, alkaline earth metal ions, an aluminum ion and an ammonium ion, or a pharmaceutically acceptable salt thereof.

6. The method according to claim 5 wherein said compound is administered in the form of a pharmaceutical composition together with a pharmaceutically acceptable carrier or diluent.

* * * * *